US008808746B2

(12) United States Patent
Woo et al.

(10) Patent No.: US 8,808,746 B2
(45) Date of Patent: Aug. 19, 2014

(54) SUSTAINED-RELEASE MICROSPHERES AND METHODS OF MAKING AND USING SAME

(75) Inventors: Byung Ho Woo, Broadview Heights, OH (US); Sumeet H. Dagar, Deerfield, IL (US); Kang Yong Yang, Flossmoor, IL (US)

(73) Assignee: Fresenius Kabi USA, LLC, Lake Zurich, IL (US)

( * ) Notice: Subject to any disclaimer, the term of this patent is extended or adjusted under 35 U.S.C. 154(b) by 1682 days.

(21) Appl. No.: 11/587,883

(22) PCT Filed: Apr. 29, 2005

(86) PCT No.: PCT/US2005/015108
§ 371 (c)(1),
(2), (4) Date: Oct. 9, 2007

(87) PCT Pub. No.: WO2005/110369
PCT Pub. Date: Nov. 24, 2005

(65) Prior Publication Data
US 2008/0131513 A1    Jun. 5, 2008

Related U.S. Application Data

(60) Provisional application No. 60/566,887, filed on Apr. 30, 2004, provisional application No. 60/647,878, filed on Jan. 28, 2005.

(51) Int. Cl.
| | |
|---|---|
| A61K 9/16 | (2006.01) |
| A61K 38/02 | (2006.01) |
| A61K 31/517 | (2006.01) |
| A61K 38/16 | (2006.01) |
| A61K 31/404 | (2006.01) |

(52) U.S. Cl.
USPC ....... 424/489; 514/259.41; 514/397; 514/414

(58) Field of Classification Search
None
See application file for complete search history.

(56) References Cited

U.S. PATENT DOCUMENTS

| | | | | |
|---|---|---|---|---|
| 5,271,945 | A | * | 12/1993 | Yoshioka et al. ........... 424/489 |
| 5,700,486 | A | * | 12/1997 | Canal et al. ................ 424/501 |
| 5,871,778 | A | * | 2/1999 | Kino et al. ................. 424/489 |
| 5,945,126 | A | * | 8/1999 | Thanoo et al. ............. 424/489 |
| 5,972,890 | A | * | 10/1999 | Lees et al. ................. 424/1.69 |
| 6,117,455 | A | | 9/2000 | Takada et al. |
| 6,156,346 | A | * | 12/2000 | Chen et al. ................ 424/489 |
| 6,287,587 | B2 | | 9/2001 | Shigeyuki et al. |
| 6,346,274 | B1 | * | 2/2002 | Koll et al. ................. 424/497 |
| 6,534,094 | B2 | * | 3/2003 | Moyano et al. ........... 424/491 |
| 6,551,578 | B2 | | 4/2003 | Adjei et al. |
| 2004/0071715 | A1 | | 4/2004 | Schwendeman et al. |
| 2005/0042294 | A1 | * | 2/2005 | Thanoo et al. ............. 424/486 |

FOREIGN PATENT DOCUMENTS

| | | |
|---|---|---|
| EP | 0 330 180 A1 | 8/1989 |
| EP | 0 330 180 B1 | 8/1989 |
| EP | 0 330 180 B2 | 8/1989 |
| EP | 0 350 246 A2 | 1/1990 |
| EP | 0 350 246 A3 | 1/1990 |
| EP | 0 350 246 B1 | 1/1990 |
| WO | WO-95/13814 A1 | 5/1995 |
| WO | WO-96/28143 A1 | 9/1996 |
| WO | WO-00/74709 A2 | 12/2000 |
| WO | WO-00/76483 A1 | 12/2000 |

OTHER PUBLICATIONS

Arana, V. et al. (Dec. 2004). "Healing of Diabetic Foot Ulcers in L-Arginine-Treated Patients," *Biomedicine and Pharmacotherapy* 58(10):588-597.

Chui, W.K. et al. (Jan.-Feb. 1997). "Prolonged Retention of Cross-Linked Trypsin in Calcium Alginate Microspheres," *Journal of Microencapsulation* 14(1):51-61.

Gilding, D.K. et al. (Dec. 1979). "Biodegradable Polymers for Use in Surgery—Polyglycolic/Poly(actic acid) Homo- and Copolymers: 1," *Polymer* 20:1459-1464.

Hora, M. S. et al. (Jul. 1990). "Release of Human Serum Albumin from Poly(lactic-co-glycolide) Microspheres," *Pharmaceutical Research* 7(11):1190-1194.

Hora, M. S. et al. (Aug. 1990). "Controlled Release of Interleukin-2 from Biodegradable Microspheres," *Bio/Technology* 8:755-758.

International Search Report mailed on Sep. 1, 2006, for PCT Patent Application No. PCT/US2005/015108 filed on Apr. 29, 2005, 4 pages.

Tabata, Y. et al. (Oct. 1988). "Macrophage Phagocytosis of Biodegradable Microspheres Composed of L-Lactic Acid/Glycolic Acid Homo- and Copolymers," *Journal of Biomedical Materials Research* 22:837-858.

\* cited by examiner

*Primary Examiner* — Susan Tran
*Assistant Examiner* — William Craigo
(74) *Attorney, Agent, or Firm* — Morrison & Foerster LLP

(57) ABSTRACT

Provided, among other things, are compositions and methods for making sustained-release microspheres, as well as a microsphere delivery system for the sustained release of an active agent. The microsphere delivery system comprises a homogeneous mixture of biodegradable polymer, active agent, and a so-called release-modifying agent (including a pH-stabilizing agent), and provides protected and sustained release of active agents from the microsphere delivery system. According to the invention, the microspheres preferably are produced by an oil-in-water emulsion method that involves the production of a homogeneous oil phase prepared by mixing active agent and a release-modifying agent, such as arginine, with biodegradable polymer, each dissolved in organic solvent. The homogeneous oil phase desirably is then dispersed in an aqueous phase containing an emulsifying agent, followed by solvent removal, to produce the microspheres in which the active agent and release-modifying agent are distributed homogeneously throughout the biodegradable polymer matrix.

22 Claims, No Drawings

SUSTAINED-RELEASE MICROSPHERES AND METHODS OF MAKING AND USING SAME

CROSS-REFERENCE TO RELATED APPLICATIONS

This application is a National Phase filing under 35 U.S.C. §371 of International Application No. PCT/US2005/015108 filed on Apr. 29, 2005, which claims priority benefit to U.S. Provisional Patent Application No. 60/647,878 filed on Jan. 28, 2005 and U.S. Provisional Patent Application No. 60/566,887 filed on Apr. 30, 2004, the contents of which are incorporated herein by reference in their entirety.

FIELD OF THE INVENTION

The invention pertains among other things to compositions and methods for making sustained-release microspheres, and to the product—a microsphere delivery system for the sustained release of an active agent—produced thereby. The microspheres of the invention preferably comprise a biodegradable polymer, and incorporate a release-modifying agent for effecting sustained delivery of active agents. According to the method of the invention, the release-modifying agents preferably are solubilized in an organic phase in which biodegradable polymer and active agent are homogeneously dissolved. More preferably, the invention relates to a composition and an oil-in-water emulsion method for preparing microspheres incorporating an active agent and a release-modifying agent.

BACKGROUND OF THE INVENTION

Biodegradable drug delivery systems (e.g., including microcapsules, microspheres, nanocapsules, nanoparticles, and biodegradable implants) are used to release drugs for an extended period of time. The biodegradable delivery systems are often prepared using biodegradable polyesters such as poly (ε-caprolactone), poly(ε-caprolactone-co-DL-lactic acid), poly(ε-caprolactone-co-glycolic acid), poly(DL-lactic acid), and poly(DL-lactide-co-glycolide).

Degradation of the polyesters [e.g., poly(DL-lactic acid), and poly(DL-lactide-co-glycolide)] has been reported to proceed by nonenzymatic random hydrolytic cleavage of ester linkages by an autocatalytic process. The biodegradable polyesters degrade slowly into acidic lower molecular weight fragments, and ultimately into lactic and glycolic acid monomers which are excreted through normal metabolic pathways. Upon incorporation of the polyesters into microspheres, acidic degradants created by polymer degradation result in an extremely acidic microenvironment in the microsphere. The acidic microenvironment induced by the polymer degradants often destabilizes and causes deterioration of the biological activity of the incorporated active substances in the microspheres.

Thus, there remains a need for a compositions and methods for improving the stability of active agents incorporated into microspheres. The invention provides such compositions and methods. These and other advantages of the present invention, as well as additional inventive features, will be apparent from the description of the invention provided herein.

BRIEF SUMMARY OF THE INVENTION

Among other things, the present invention provides a method for incorporating release-modifying agents and active agents (e.g., drug substances) into biodegradable microspheres, as well as a formulation for effecting sustained release of active agent, and that preferably protects the incorporated active agent from biodegradable polymer matrix degradants.

Biodegradable microspheres incorporating release-modifying agents for delivery of active agents, and methods for their preparation and administration, are provided. Release-modifying agents include pH-stabilizing agents, which are agents or mixtures of agents, that, by their presence, resist changes in pH upon the addition of small amounts of acid or alkali. Exemplary release-modifying agents include basic amino acids, such as L-arginine, optionally mixed with organic acid, such as glacial acetic acid. The microspheres incorporating L-arginine show improved stability of the active agent comprising the microspheres. In a preferred embodiment, the microspheres comprise biodegradable polymer, active agent and release-modifying agent, which are prepared using an oil-in-water (O/W) emulsion technique. The microspheres incorporating a release-modifying agent can be used among other things for enhancing systemic or local delivery of active agent to human or animal for a prolonged period of time.

DETAILED DESCRIPTION OF THE INVENTION

The present invention provides a microsphere delivery system for the sustained release of an active agent (as defined herein, e.g., a therapeutic and/or diagnostic agent) either in vivo or in vitro. The microsphere delivery system according to this invention preferably can be used to administer a wide variety of active agents in different molecular weights such as steroids, vaccines, vitamins, enzymes, analgesic, antibiotics, antineoplastics, hormones, and peptide and proteins drugs, to name but a few.

The "microspheres" according to the invention include nanospheres; the microspheres generally have a uniform shape and preferably range in size from about 0.1 microns to about 500 microns in diameter, even more preferably from about 0.1 micron to about 150 microns, especially from about 1.0 microns to about 500 microns, and particularly from about 1.0 microns to about 150 microns, depending upon the fabrication conditions. The microspheres can be employed as a "delivery system" to release active agent from the microsphere (e.g., from the interior of the microsphere, as well as from the exterior of the microsphere, as for a surface-associated drug), when placed in an appropriate aqueous medium (e.g., such as in body fluids, in a physiologically acceptable buffer, or in any appropriate aqueous environment). The microspheres of the invention are advantageous as a delivery system since, among other things, they show improved stability and release conditions for the active agent as compared, e.g., to previously-described microspheres. Preferably this delivery is effected over a prolonged period of time, thereby providing sustained release of the active agent.

As used herein, the term "sustained-release" refers to the release of an active agent from the microspheres of the invention over a defined or extended period of time in a continuous, discontinuous, linear or nonlinear manner. For example, release may be essentially biphasic, e.g., as where the release includes an initial release or so-called "burst" (even a controlled or suppressed release that is relatively low) of active agent from the microsphere, followed by relatively continuous release of the active agent from the microsphere over time. Preferably the initial release is less than about 50% of active agent released from the microsphere in twenty four hours, even more preferably less than about 40%, still even more preferably less than about 30%, and most preferably is less than about 25%. Methods of measuring release are well known in the art (see, e.g., Hora et al., Pharm. Res. 7:1190-1194 (1990); Hora et al., Bio/Technology 8:755-758 (1990)). The precise amount of time over which the active agent continues to be released from the microspheres of the invention depends on the characteristics of the active agent being released and the parameters used to form the microspheres, and may be longer than, roughly the same length as, or shorter than that of release from comparable microspheres (e.g., conventional microspheres) that do not contain the release-modifying agent of the invention, but preferably (e.g., given the more linear release rate) is the same length as, or is shorter than, that of release from conventional microspheres. Preferably according to the invention sustained release is continuous, is linear, and is prolonged (i.e., as opposed to being short-lived, as in the case of a pronounced initial burst).

Sustained release according to the invention is effected by the unique interplay of the components of the novel microsphere delivery system, and primarily by the interaction of the release-modifying agent, the biodegradable polymer, and the active agent comprising the microspheres. These components are further described below. In particular, a microsphere delivery system for sustained release of an active agent according to the invention preferably comprises a biodegradable polymer, an active agent, and a release-modifying agent, optimally wherein the release-modifying agent stabilizes the active agent and enhances its sustained release. The microsphere delivery system preferably comprises a homogeneous mixture of the biodegradable polymer, active agent and release-modifying agent, particularly one wherein the active agent and release-modifying agent are evenly (e.g., homogeneously) distributed in and throughout the matrix of the biodegradable polymer. The microspheres of the invention (e.g., as compared to other microspheres and/or microcapsules) optimally are of a uniform (or near uniform) structure and composition throughout.

Release-Modifying Agent

In particular, the "release-modifying agent" is that component which stabilizes the active agent and/or enhances its sustained release from the microsphere. To some extent, these characteristics can merge and become indistinguishable given that they appear to stem from the same underlying phenomenon. To "stabilize" the active agent means that the active agent shows increased stability in the presence of the release-modifying agent, or in a microsphere containing the release-modifying agent, as compared to in the absence of the release-modifying agent, or in a microsphere in which the release-modifying agent is not present. Without being bound by any theory, the release-modifying agent may modulate, for example, may reduce or increase the interaction between the active agent and biodegradable polymer. Preferably the release-modifying agent of the invention reduces the interaction between the active agent and biodegradable polymer.

Stability can be assessed by a variety of means known in the art, but a preferred measure of stability according to the invention is the purity or potency of the active agent at any time contained within a microsphere delivery system of the invention that also includes the release-modifying agent, as compared to the purity or potency of the active agent at the comparable time contained within a comparable microsphere delivery system that does not include the release-modifying agent of the invention. "Purity" of the active agent as a measure of stability can be determined, for example, by high performance liquid chromatography (HPLC) or a similar method. HPLC allows the separation of pure active agent from impurities including but not limited to degradation products such that the purity can be quantitated by determining the peak area of the pure active agent as compared to the total peak area of the sample being assessed (e.g., the ratio of pure active agent and total peak area). "Potency" of the active agent as a measure of stability can be determined, for example, by measuring the quantity (e.g., amount, concentration or other measure) and/or biological activity of the active agent according to any suitable method known to a skilled person.

In the presence of release-modifying agent (e.g., when such release-modifying agent comprises the microspheres of the invention), the amount of the active agent interacted with biodegradable polymer by means of any physical or chemical interaction (e.g. hydrophilic, hydrophobic, ionic and non-ionic interaction, and adsorption, absorption), or other interaction, within from about 1 to about 24 hours of contact of the microspheres with appropriate aqueous medium, preferably is less than about 20% (e.g., from about 0.01% to about 20%), even more preferably is less than about 10% (e.g., from about 0.01% to about 10%), and more desirably is less than about 5% (e.g., from about 0.01% to about 5%), of the total amount of active agent. Even more preferably, the amount of the active agent interacted with biodegradable polymer increases up to not more than about 30% after continuous contact of the active agent with the biodegradable polymer (e.g., in the microsphere delivery system of the invention present in an appropriate aqueous medium) for up to about 7 days. Preferably the release-modifying agent allows the active agent to remain in intact form in the presence of biodegradable polymer in the microsphere delivery system of the invention. Preferably, in the microspheres of the invention, from about 85% to up to about 100% of the initial amount of the active agent remains intact after up to about 24 hours of contact with the biodegradable polymer, and from about 50% up to about 100% of the initial amount of the active agents remains intact after up to about 7 days of contact with the biodegradable polymer.

Preferably the release-modifying agent of the microsphere delivery system of the invention also "enhances sustained release" of the active agent. By this it is meant that the release-modifying agent of the invention provides for release that is controlled, e.g., as opposed to being haphazard, e.g., with an uncontrollable rate of release. The release-modifying agent of the invention preferably enhances (i.e., increases or augments) sustained release in that it allows for controlled and more gradual release of an active agent from the polymeric microspheres of the invention. In particular, the release-modifying agent of the invention preferably enhances sustained release by allowing the microspheres of the invention to be employed to release active agent without an initial burst or rapid release of the active agent being observed, or at the very least with a reduced initial burst/release of the active agent as compared to the initial burst/release observed using comparable microspheres that do not contain the release-modifying agent of the invention. Separate and apart from any effect on initial release, preferably the release-modifying agent of the invention enhances sustained release by providing for more linear release of the active agent than from conventional microspheres which do not contain the release-modifying agent. The amount of the active agent initially released in the time period of from about 1 to about 24 hours preferably ranges from about 0.1% to about 50% of the total active agent incorporated in the microspheres, especially from about 0.1% to about 40%, even more preferably from about 0.1% to about 30%, still even more preferably from about 0.1% to about 25%, and in another preferred embodiment about 0.1% to about 15%.

As indicated previously, the release-modifying agent can be a pH-stabilizing agent. The "pH-stabilizing agent" is that component which maintains the pH of microspheres such that the change of pH of the polymer matrix in the aqueous environment decreases or is minimized in the presence of the pH-stabilizing agent, or in a microsphere containing the pH-stabilizing agent, as compared to in the absence of the pH-stabilizing agent, or in a microsphere in which the pH-stabilizing agent is absent. Thus, a release-modifying agent which is a pH-stabilizing agent enhances (i.e., increases or augments) sustained release in that preferably it allows for maintenance of a more stable pH within the microsphere. The pH-stabilizing agents are agents or mixtures of agents that, by their presence in solution, resist changes in pH upon the addition of small amounts of acid or alkali, and thus act as so-called "buffers". This resistance to a change in pH is known as "buffer action". Buffers consist of a weak acid and its conjugate base, or a weak base and its conjugate acid. Thus, in particular, a pH-stabilizing agent (release-modifying agent) preferably comprises a mixture of acid and base (particularly acid and its conjugate base, or base and its conjugate acid), so-called acidic and basic "counterparts."

Exemplary release-modifying agents (including pH stabilizing agents) according to the invention include basic amino acids, such as arginine (especially L-arginine), which is preferred. Exemplary release-modifying agents include mixtures of arginine and organic acids, especially glacial acetic acid. The mixture of arginine and glacial acetic acid is preferred according to the invention. This mixture appears to be a pH stabilizing agent. Other pH stabilizing agents (e.g., buffers) include but are not limited to agents or mixture of agents such as acetate, tartrate, glutamate, citrate, benzoate, lactate, gluconate, phosphate, glycine, leucine, arginine, and lysine.

Arginine is a basic amino acid that is strongly alkaline in aqueous solution, and glacial acetic acid is a weak acid that is acidic in aqueous solution. Mixing of arginine and glacial acetic acid forms a buffer capable of resisting a pH change. Without wishing to be bound by any theory, it appears that incorporating arginine in the polymeric microspheres of the invention (especially arginine mixed with glacial acetic acid) neutralizes or buffers the acidic hydrolysates of the polymer, which hydrolysates are believed to promote degradation of the active agent. As a result, arginine (especially arginine mixed with glacial acetic acid) appears to protect the incorporated active agent from the deleterious impact of the acidic polymer fragments present in the microspheres. Also, it appears that release-modifying agents (e.g., pH-stabilizing agents) may reduce the ionic interaction between the relatively negatively charged acid moiety of polymer and any relatively positively charged moiety that may exist on the active agent (e.g., the drug substance). This ionic interaction often results in an extended lag time between the initial diffusional release and erosion-mediated drug release. Thus, again without wishing to be bound by any theory, it appears that in some situations, release-modifying agents (e.g., pH-stabilizing agents) interact with the polymer (instead of the polymer interacting with the active agent) and thereby reduce or prevent the active agent/polymer interaction. Consequently, and regardless of whether this is the actual mechanism, release-modifying agents (e.g., pH-stabilizing agents) allow more gradual and/or controlled release of active agent (e.g., drug substance) from the polymeric microspheres of the invention.

It is known in the art that arginine can be employed as a therapeutically significant agent (for instance, for wound healing; see, e.g., Arana et al., Biomed. Pharmacother., 58(10):588-597 (2004)), as a stabilizing or cryoprotectant agent in microspheres (see, e.g., U.S. Pat. No. 6,287,587), or to itself form a cross-linked microsphere (see, e.g., Chui et al., J. Microencapsulation, 14(1):51-61 (1997)). Such known therapeutic uses of arginine either require relatively large amounts of arginine in order to achieve the desired effect, and/or do not have the active agent and arginine evenly distributed in and throughout a polymer matrix (especially a microsphere polymer matrix). The present invention differs from the art among other matters in that inclusion of a small amount of arginine or other release-modifying agent (including arginine in mixture with glacial acetic acid) in the microspheres according to the invention is surprisingly able to modify the release of active agent from the microspheres. In particular, arginine or other release-modifying agent (including arginine in mixture with glacial acetic acid) preferably is employed in the present inventive microspheres in a reduced amount over the arginine used in these other applications. Namely, preferably arginine, other release-modifying agent, or the basic counterpart of a pH-stabilizing agent is included in an amount (w/w) of less than about 1%, more preferably in an amount (w/w) of less than about 0.7%, less than about 0.8%, or less than about 0.9%. Even more preferably arginine, other release-modifying agent, or the basic counterpart of the pH-stabilizing agent preferably is contained within the microspheres in an amount (w/w) ranging from about 0.5% to about 0.7%, especially in an amount (w/w) of about 0.55%, about 0.60%, about 0.65%, or about 0.7%. Preferably the acidic counterpart of a pH-stabilizing agent, such as glacial acetic acid, is included in an amount (w/w) of less than about 5%, more preferably in an amount (w/w) of less than about 3%, less than about 3.5%, or less than about 4.0%. Even more preferably the acidic counterpart of the pH-stabilizing agent is contained within the microspheres in an amount (w/w) ranging from about 1% to about 4%, especially in an amount (w/w) of about 1.5%, about 2.0%, about 2.5%, or about 3.0%.

Arginine is available primarily in either of two chemical conformations, e.g., arginine-free base, or as its salt, e.g., arginine hydrochloride. Arginine-free base and its hydrochloride salt are soluble in water. By comparison, both are practically insoluble in organic solvents. In particular, arginine hydrochloride is only slightly soluble in hot alcohol. To prepare microspheres using the oil-in-water (O/W) emulsion technique, preferably an oil phase is prepared comprising biodegradable polymer, active agent and release-modifying agent, e.g., L-arginine dissolved in a small volume of organic solvent. Therefore, the effective amount of arginine optimally is solubilized in a small volume of organic solvent, such as methanol acidified with acetic acid or a weak organic acid like glacial acetic acid, or such as glacial acetic acid alone. The arginine solution in organic solvent desirably is then mixed with a solution comprising the biodegradable polymer and active agent (e.g., drug substance) to form a homogeneous dispersed phase. The homogeneous dispersed phase preferably is emulsified into aqueous surfactant solution to form an O/W emulsion.

While arginine (e.g., mixed with glacial acetic acid) is preferred for use in the microsphere delivery system of the invention, other amino acids (e.g., and their salts), optionally also can be employed as release-modifying agents, either alone, or mixed with an acidic counterpart. Particularly preferred for use are amino acids which are compatible with the other components of the microspheres (e.g., with the biodegradable polymer discussed below), and are physiologically acceptable. Such other amino acids include but are not limited to basic amino acids such as lysine and histidine. Other neutral and acidic amino acids also can be used. Additionally, natural or synthetic polypeptides and macromolecules containing at least a single basic amino acid residue, or an acidic amino acid residue can be employed as a release-modifying agent. Furthermore, organic bases, such as triethylamine, diethanolamine, and N-methylglucamine optionally can be employed as a release-modifying agent. The release-modifying agents according to the invention can be used separately, or in appropriate combination. Further, such release-modifying agents desirably are capable of reducing the interaction between biodegradable polymer and active agent.

Moreover, while glacial acetic acid is preferred for use in the microsphere delivery system of the invention, other organic and inorganic acids (e.g., and their salts), optionally also can be employed as a pH-stabilizing agent (or the acidic counterpart thereof), especially acids which are compatible with the other components of the microspheres (e.g., with the biodegradable polymer discussed below), and are physiologically acceptable. Such other acids include but are not limited to weak organic acids (such as, e.g., citric acid, tartaric acid, succinic acid, lactic acid, glycolic acid, glutamic acid, and benzoic acid), and inorganic acids (such as, e.g., hydrochloric acid, phosphoric acid, nitric acid, carbonic acid, and sulfuric acid). These pH-stabilizing compounds may be used separately or in combination (e.g., combined together, and/or in combination with their basic counterpart).

It goes without saying, and would be understood by one of ordinary skill in the art that the pH of the microspheres can also be adjusted by, and is impacted by, the pH-stabilizing agents. The pH of microsphere without pH-stabilizing agents included necessarily may vary depending on the composition of microspheres. For instance, the microspheres prepared with a large quantity of basic active agent may show higher pH than microspheres prepared with an acidic active agent. Also, the pH may vary with the concentration or amount of the active drug employed, the acidic monomers contained within the polymer, and the intrinsic acidity of polymer itself. However, with use of pH-stabilizing agents, the pH of the microsphere can be controlled by the inclusion of different amounts and/or different species of acid and/or base. Exemplary microspheres containing octreotide as the active agent and arginine with glacial acetic acid as the pH-stabilizing agents maintain the pH of between about 3 and about 5, at which pH octreotide maintains better stability than lower or higher pH levels. The target pH of the microsphere accordingly may be adjusted to provide the optimum pH to ensure stability of the active agent. For example, with an active agent that is stable within a neutral pH range, a pH-stabilizing agent which has buffering capacity within the neutral pH range (e.g., phosphate) can be employed. Likewise, with an active agent that is stable within a very low pH range (e.g., pH<3), a pH-stabilizing agent which has buffering capacity at pH<3.0 (e.g., Glycine-HCl buffer) can be used.

Biodegradable Polymer

Another key component of the microsphere delivery system of the invention is the polymer. According to the invention, a "polymer" preferably is a biodegradable polymer, especially a polyester. Examples of monomers used to form such a polyester include, but are not limited to, lactic acid (alpha-hydroxyproprionic acid), glycolic acid (alpha-hydroxyacetic acid), an ϵ-caprionic acid, an ϵ-caproic acid, p-dioxanone, alkylene oxylate, cycloalkylene, alkylene succinate, and 3-hydroxy butyrate. The aforementioned polyesters are particularly suited for the methods and compositions of the present invention because of their characteristically low human toxicity and virtually complete biodegradability.

Preferred of such polyesters for use herein are polyglycolic (PGA) and polylactic (PLA) acids, and copolymers of glycolic acid and lactic acid (e.g., D,L-lactic acid) (PLGA). These polymers are available in a variety of molecular weights, and the appropriate molecular weight to provide the desired release rate for the active agent in question can be readily determined by one of ordinary skill in the art. Thus, for instance, for PLA, a suitable molecular weight preferably is on the order of from about 2000 to 250,000 daltons. For PLGA, suitable molecular weights desirably range from about 5,000 to about 200,000 daltons, preferably from about 7,000 to about 150,000 daltons, and most preferably from about 10,000 to about 100,000 daltons. In a particularly preferred embodiment according to the invention, the polymer preferably comprises a molecular weight of from about 12,000 to about 50,000 daltons.

If a copolymer such as PLGA is used to form the microspheres, a variety of lactic acid:glycolic acid ratios are applicable herein, and the ratio is largely a matter of choice, depending in part on the rate of degradation desired. For example, a 50:50 PLGA polymer, containing 50% D,L-lactide and 50% glycolide, will provide a fast resorbing copolymer while 75:25 PLGA degrades more slowly, and 85:15 and 90:10, even more slowly, due to the increased lactide component. It is readily apparent that a suitable ratio of lactide:glycolide is easily determined by one of skill in the art based on the nature disorder to be treated. Moreover, mixtures of microspheres with varying lactide:glycolide ratios can be employed in the formulations of the invention in order to achieve the desired release kinetics.

Preferably according to the invention, the biodegradable polymer is a copolymer of lactic acid and glycolic acid (i.e., is a PLGA copolymer) with unit proportions ranging from 40:60 to 75:25, and especially with unit proportions ranging from 50:50 (i.e., is 50:50 poly(D,L-lactide-co-glycolide or PLGA copolymer), or is a mixture of a separate polymers of lactic acid and glycolic acid.

The foregoing exemplary polymers suitable for use in the present invention are, of course, either readily available commercially (e.g., from Boehringer Ingelheim, Germany and Birmingham Polymers, Inc., Birmingham, Ala.), or are obtainable by condensation polymerization reactions from the suitable monomers or, comonomers or oligomers. For instance, homopolymers and copolymers of glycolic and lactic acids can be prepared by direct poly-condensation or by reacting glycolide and lactide monomers (see, e.g., Gilding et al., "Biodegradable Polymers for Use in Surgery—Polyglycolic/Poly(lactic acid) Homo- and Copolymers: 1", Polymer, 20, 1459 (1979), and Tabata et al., J. Biomed. Mater. Res., 22, 837-858 (1988)).

Active Agent

Still another key component of the microsphere delivery system of the invention is the active agent. As used herein, an "active agent" refers to an agent which has a diagnostic or therapeutic activity. Accordingly, an active agent can include a detectable label (e.g., a radioactive label) that is useful for identifying the location of the released agent in vivo. Active agents also include therapeutic agents which are useful for treating a disease, disorder or condition (e.g., are so-called biologically active substances, or physiologically active agents). Preferably the active agent is selected from the group consisting of peptides, proteins, lipids, polysaccharides, and nucleic acids. Even more preferably, the biologically active substance is a peptide or protein.

The active agents of the invention typically can be further divided into categories, based upon the activity of the agent or the type of disease, disorder or condition that is being treated. Some broad categories of active agents (e.g., physiologically active agents or biologically active substances) which can be used in the present invention include, but are not limited to, analgesics, anesthetics, antiallergic agents, antiarrythmic agents, antibiotics, antibodies, anticoagulants, antidementia agents, antidepressants, anti-psychotics, antidiabetic agents, antiinfective agents, anti-inflammatory agents, antigens, antineoplastics, antipyretics, antitumoral agents, antiulcer agents, antiviral agents, carbohydrates and polysaccharides, cardiotonics, chemotherapeutic agents, cholesterol lowering agents, conjugates or complexes of small molecules and proteins or mixtures thereof, cytokines, enzymes, growth factors, hematopoietics, hormones, hypotensive diuretics, immunological agents and adjuvants, immunomodulating agents, neuroactive agents, nucleotides and nucleic acids, organic or inorganic synthetic pharmaceutical agents, osteoporosis therapeutic agents, psychotropic agents, psychotropic agents, thrombopoietics, vaccines, vasoactive agents, viruses and virus particles, and the like.

The active agents of the invention include protein or peptide agents (collectively, "peptide agents"), as well as non-protein or non-peptide agents (collectively, "non-peptide agents"). The various peptide agents for use herein include not only the naturally occurring proteins or peptides themselves but also pharmacologically active derivatives and analogs thereof. Exemplary non-peptide agents include the following non-limiting categories of agents: (a) nucleotides and nucleic acids; (b) carbohydrates and polysaccharides; (c) viruses and virus particles; (d) conjugates or complexes of small molecules and proteins, or mixtures thereof; and (e) organic or inorganic natural or synthetic pharmaceutical agents (e.g., so-called drugs).

The preferred peptide agents (active agents) include but are not limited to peptide hormones, cytokines, growth factors, factors acting on the cardiovascular system, factors acting on the central and peripheral nervous systems, factors acting on humoral electrolytes and humoral organic substances, factors acting on bone and skeleton, factors acting on the gastrointestinal system, factors acting on the immune system, factors acting on the respiratory system, factors acting on the genital organs, enzymes, and the like.

Exemplary active agents according to the invention are set out as follows.

Exemplary hormones include but are not limited to insulin, growth hormone, parathyroid hormone, luteinizing hormone-releasing hormone (LHRH), adrenocorticotropic hormone (ACTH), amylin, oxytocin, luteinizing hormone, nafarelin acetate, leuprolide acetate, follicle stimulating hormone, glucagon, prostaglandins, PGE1, PGE2 and other factors acting on the genital organs and their derivatives, analogs and congeners, and the like.

Exemplary antibiotics include but are not limited to tetracycline, aminoglycosides, penicillins, cephalosporins, sulfonamides, chloramphenicol sodium succinate, erythromycin, vancomycin, lincomycin, clindamycin, nystatin, amphotericin B, amantidine, idoxuridine, p-amino salicylic acid, isoniazid, rifampin, antinomycin D, mithramycin, daunomycin, adriamycin, bleomycin, vinblastine, vincristine, procarbazine, imidazole, carboxamide, and the like.

Exemplary hematopoietic or thrombopoietic factors include but are not limited to erythropoietin, granulocyte colony stimulating factor (G-CSF), granulocyte-macrophage stimulating factor (GM-CSF) and macrophage colony stimulating factor (M-CSF), leukocyte proliferation factor preparation (Leucoprol, Morinaga Milk), thrombopoietin, platelet proliferation stimulating factor, megakaryocyte proliferation (stimulating) factor, factor VIII, and the like.

Exemplary antidementia agents include but are not limited to Selegelene.

Exemplary antiviral agents include but are not limited to amantidine and protease inhibitors.

Exemplary antitumoral agents include but are not limited to doxorubicin, epirubicin, idarubicin, daunorubicin, taxol, and methotrexate.

Exemplary antipyretics and analgesics include but are not limited to aspirin, Motrin®, Ibuprofin, Naprosyn®, Indocin®, acetaminophen, and the like.

Exemplary anti-inflammatory agents include but are not limited to NSAIDS, aspirin, steroids, cox-2 inhibitors, dexamethasone, hydrocortisone, prednisolone, and the like.

Exemplary antiulcer agents include but are not limited to famotidine, cimetidine, nizatidine, ranitidine, and sucralfate.

Exemplary antiallergic agents include but are not limited to antihistamines, diphenydramine, loratadine, and chlorpheniramine.

Exemplary antidepressants and psychotropic agents include but are not limited to lithium, amitriptyline, tricyclic antidepressants, fluoxetine, PROZAC®, and paroxetine.

Exemplary anti-psychotic agents include RISPERDAL CONSTA® (risperidone).

Exemplary cardiotonics include digoxin and others.

Exemplary antiarrhythmic agents include metoprolol and procainamide and others.

Exemplary vasodilators include but are not limited to nitroglycerin, nifedipine, and isosorbide dinitrate.

Exemplary diuretics include hydrochlorothiazide and furosemide, as well as others.

Exemplary antihypertensive agents include but are not limited to captopril, nifedipine, and atenolol.

Exemplary antidiabetic agents include but are not limited to glucozide, chloropropamide, metformin, and insulin.

Exemplary anticoagulants include but are not limited to warfarin, heparin, and Hirudin.

Exemplary cholesterol lowering agents include but are not limited to lovastatin, cholestyramine, and clofibrate.

Exemplary therapeutic agents for treating osteoporosis and other factors acting on bone and skeleton include but are not limited to calcium, alendronate, pamidronate, bone GLa peptide, parathyroid hormone and its active fragments (e.g., osteostatin), histone H4-related bone formation and proliferation peptide (e.g., OGP), and other agents.

Exemplary enzymes and enzyme cofactors include but are not limited to: pancrease, L-asparaginase, hyaluronidase, chymotrypsin, trypsin, tPA, streptokinase, urokinase, pancreatin, collagenase, trypsinogen, chymotrypsinogen, plasminogen, streptokinase, adenyl cyclase, and superoxide dismutase (SOD).

Exemplary vaccines include but are not limited to Hepatitis B, MMR (measles, mumps, and rubella), and Polio vaccines.

Exemplary immunological adjuvants include but are not limited to Freunds adjuvant, muramyl dipeptides, concanavalin A, BCG, and levamisole.

Exemplary cytokines include but are not limited to lymphokines, monokines, hematopoietic factors and the like. Lymphokines and cytokines useful in the practice of the invention include interferons (e.g., interferon-alpha, -beta and -gamma), interleukins (e.g., interleukin 2 through 11) and the like. Monokines useful in the practice of the invention include interleukin-1, tumor necrosis factors (e.g., TNF-alpha and -beta), malignant leukocyte inhibitory factor (LIF) and the like.

Exemplary growth factors include but are not limited to nerve growth factors (NGF, NGF-2/NT-3), epidermal growth factor (EGF), fibroblast growth factor (FGF), insulin-like growth factor (IGF), transforming growth factor (TGF), platelet-derived cell growth factor (PDGF), hepatocyte growth factor (HGF) and the like.

Exemplary factors acting on the cardiovascular system include but are not limited to factors which control blood pressure, arteriosclerosis, etc., such as endothelins, endothelin inhibitors, and endothelin antagonists, endothelin producing enzyme inhibitors vasopressin, renin, angiotensin I, angiotensin II, angiotensin III, angiotensin I inhibitors, angiotensin II receptor antagonists, atrial naturiuretic peptide (ANP), antiarrhythmic peptide and the like.

Exemplary factors acting on the central and peripheral nervous systems include but are not limited to opioid peptides (e.g., enkephalins, endorphins), neurotropic factor (NTF), calcitonin gene-related peptide (CGRP), thyroid hormone releasing hormone (TRH), salts and derivatives of TRH, neurotensin and the like.

Exemplary factors acting on the gastrointestinal system include secretin and gastrin, as well as others.

Exemplary factors acting on humoral electrolytes and humoral organic substances include but are not limited to factors which control hemaglutination, plasma cholesterol level or metal ion concentrations, such as calcitonin, apoprotein E and hirudin, as well as laminin and intercellular adhesion molecule 1 (ICAM-1), which represent exemplary cell adhesion factors.

Exemplary factors acting on the kidney and urinary tract include but are not limited to substances which regulate the function of the kidney, such as brain-derived natriuretic peptide (BNP), urotensin and the like.

Exemplary factors which act on the sense organs include factors which control the sensitivity of the various organs, such as substance P.

Exemplary factors acting on the immune system include but are not limited to factors which control inflammation and malignant neoplasms and factors which attack infective microorganisms, such as chemotactic peptides and bradykinins.

Exemplary factors acting on the respiratory system include factors associated with asthmatic responses, and the like.

Also included are naturally occurring, chemically synthesized or recombinant peptides or proteins which may act as antigens, such as cedar pollen and ragweed pollen. These factors are administered, either independently, coupled to haptens, or together with an adjuvant, in the formulations according to the present invention.

While specific examples of active agents for use in accordance with this invention are mentioned herein, this does not mean that other agents are excluded. Particularly preferred according to the invention is an active agent selected from the group consisting of calcitonin (e.g., especially salmon calcitonin), octreotide, Zoladex® (Goserelin), lupron (Leuprolide), human growth hormone, and Octastatin. Calcitonin for use in the present invention preferably includes not only naturally-occurring products such as salmon calcitonin, human calcitonin, porcine calcitonin, eel calcitonin and chicken calcitonin, but also analogs and synthetic variations of calcitonin.

Microspheres

The present invention also provides a process for preparing a microsphere delivery system as described herein that comprises biodegradable polymer, active agent, and release-modifying agent. The microspheres according to the invention preferably contain a homogeneous mixture of biodegradable polymer, active agent and release-modifying agent wherein these components are evenly distributed in the polymer matrix.

The process of preparation according to the invention preferably comprises the steps of:

(a) dissolving a biodegradable polymer in a first organic solvent that is immiscible with water to produce a first mixture;

(b) dissolving an active agent in a second organic solvent that is miscible with water to produce a second mixture;

(c) producing a third mixture by separately dissolving a release-modifying agent in either (i) a third organic solvent that is miscible with water, or (ii) a mixture of the second organic solvent and third organic solvent;

(d) mixing together the first mixture, second mixture and third mixture to prepare a homogeneous organic dispersed phase;

(e) emulsifying the homogeneous organic dispersed phase to produce microdroplets; and (f) removing the solvent (e.g., first organic solvent, second organic solvent, and third organic solvent) from the microdroplets to produce the microspheres.

As indicated above, the present inventive method optimally employs one or more organic solvents, which (along with the biodegradable polymer, active agent, and release-modifying agent) preferably are pharmaceutically or pharmacologically acceptable. By "pharmaceutically acceptable" or "pharmacologically acceptable" is meant a material which is not biologically or otherwise undesirable, i.e., the material may be administered to a being or individual along with or as part of the microsphere formulations without causing any unnecessary undesirable biological effects or interacting in a deleterious manner with any of the components of the composition in which it is contained.

According to the invention, the "first organic solvent" in which the biodegradable polymer is dissolved to produce the first mixture preferably is immiscible with water, and preferably is a volatile solvent. Examples of organic solvents that can be employed include halogenated hydrocarbons (e.g., dichloromethane, chloroform, chloroethane, trichloroethane, carbon tetrachloride, and the like), alkyl ethers having 3 or more carbon atoms (e.g., isopropylether), carboxylic acid alkyl (having 4 or more carbon atoms) esters (e.g., butyl acetate), aromatic hydrocarbons (e.g., benzene, toluene, xylene), as well as others. These solvents can be used alone or in combinations thereof. The halogenated hydrocarbons (e.g., dichloromethane, chloroform, chloroethane, trichloroethane, carbon tetrachloride, etc.) are preferred, and in particular, dichloromethane is especially preferred for the first organic solvent.

Preferably the polymer is dissolved in a small amount of the first organic solvent, reflective of its weight in the microsphere ultimately obtained. For example, the biodegradable polymer is present in the microspheres in an amount preferably ranging from about 0.2 to about 10,000 times (by weight), and even more preferably ranging from about 1 to about 1,000 times (by weight) relative to the weight of the active agent. The amount (w/w) of biodegradable polymer in the first organic solvent preferably is from about 0.5% to about 90%, more preferably from about 2% to about 60%, and most preferably from about 5% to about 50%.

The "second organic solvent" in which the active agent is dissolved to produce the second mixture desirably is miscible with water, and preferably is a non-volatile solvent. Desirably the second organic solvent also is miscible with the first organic solvent. The second organic solvent preferably includes but is not limited to the solvents methanol, ethanol, dimethylacetamide (DMA), tetrahydrofuran (THF), dioxane, dimethylsulfoxide (DMSO), and dimethylformamide (DMF). In a preferred embodiment, the second organic solvent is methanol or ethanol.

Preferably the active agent is dissolved in a small amount of the second organic solvent, reflective of its weight in the microsphere ultimately obtained. For example, the active agent is present in the microspheres in an amount (w/w) that preferably ranges from about 0.1% to about 90%, and more preferably ranges from about 1% to about 50%. The amount of the active agent in the second organic solvent preferably ranges from about 0.1 mg/mL to about 1000 mg/mL, more preferably from about 1 mg/mL to about 500 mg/mL, and most preferably from about 5 mg/mL to about 500 mg/mL.

The "third organic solvent" in which the release-modifying agent is dissolved preferably is miscible with water, and desirably is a non-volatile solvent. Desirably the third organic solvent is miscible with the second organic solvent. If the third organic solvent is not miscible with water (or even if this solvent is miscible, but it is otherwise desired), a mixture of the second organic solvent and third organic solvent can be used, e.g., instead of using the third organic solvent alone. The third organic solvent preferably includes but is not limited to the solvents alcohols (e.g., methanol, ethanol, propyl alcohol, isopropyl alcohol, and the like), acetone, acetonitrile, and acetic acid (e.g., glacial acetic acid). Preferably the third organic solvent is acetic acid, or a mixture of acetic acid and methanol. Along these lines, the third organic solvent itself in some cases might be identical to, or considered part of, the release-modifying agent, for instance, where the third organic solvent comprises the acidic counterpart to a basic counterpart of a pH-stabilizing agent. In a preferred embodiment, the release-modifying agent is arginine base, and the effective amount of arginine base preferably is dissolved in a small volume of organic solvent, such as methanol, which optimally has been acidified with a weak organic acid, such as acetic acid.

Preferably the release-modifying agent is dissolved in a small amount of the third organic solvent, reflective of its weight in the microsphere ultimately obtained. For example, the release-modifying agent preferably is present in the microspheres in an amount of less than about 1% (w/w) relative to the total microsphere mass, more preferably in an amount of less than about 0.7% (w/w), less than about 0.8% (w/w), or less than about 0.9% (w/w). Even more preferably, arginine (including arginine in admixture with glacial acetic acid), other release-modifying agent, or the basic counterpart of a pH-stabilizing agent is contained within the microspheres in an amount ranging from about 0.5% (w/w) to about 0.7% (w/w), especially in an amount of about 0.55% (w/w), about 0.60% (w/w), about 0.65% (w/w), or about 0.7% (w/w). In terms of its concentration in solvent, preferably the amount of the release-modifying agent ranges from about 0.1 to about 500 mg/mL. The amount of the third solvent employed for dissolution of the release-modifying agent preferably is from about 0.1% (v/v) to about 30% (v/v) relative to the volume of the second solvent, more preferably from about 1% to about 10% (v/v). Preferably the acidic counterpart of a pH-stabilizing agent, such as glacial acetic acid, is included in an amount (w/w) of less than about 5%, more preferably in an amount (w/w) of less than about 3%, less than about 3.5%, or less than about 4.0%. Even more preferably the acidic counterpart of the pH-stabilizing agent is contained within the microspheres in an amount (w/w) ranging from about 1% to about 4%, especially in an amount (w/w) of about 1.5%, about 2.0%, about 2.5%, or about 3.0%.

The release-modifying agent in the third organic solvent mixture (e.g., arginine in glacial acetic acid) is then mixed with the first and second mixture comprising polymer and active agent, respectively, to form a homogeneous organic dispersed phase. The "homogeneous organic dispersed phase" is a clear solution in which the solutes in the solution cannot be separated by physical separation methods, such as by conventional centrifugation and filtration—although they can be separated by ultrafiltration. To the homogeneous organic dispersed phase, hydrochloric acid, citric acid, malic acid, tartaric acid, sodium hydroxide, potassium hydroxide and/or other acids as described herein optionally can be added for pH adjustment. The pH of the homogeneous organic dispersed phase (e.g., which is the pH of the resultant microspheres) preferably ranges from about 1 to about 7, more preferably is a pH of 7 or less, most preferably the pH ranges from about 3 to about 6.5, and a pH of about 3.0, about 3.5, about 4.0, about 4.5, about 5.0, about 5.5, about 6.0 or about 6.5 is particularly preferred.

The homogeneous organic dispersed phase preferably is emulsified into aqueous surfactant solution to form an oil-in-water (O/W) emulsion. The emulsification can be carried out by conventional dispersion techniques such as intermittent shaking, mixing by means of a mixer (e.g., propeller agitator, turbine agitator, or other), colloid mill operation, mechanical homogenization, ultrasonication, and the like.

Preferably the emulsification is done in an aqueous continuous phase containing a surfactant, especially polyvinyl alcohol (PVA) in water. Examples of other emulsifiers that optionally can be employed include anionic surfactants (e.g., sodium oleate, sodium stearate, sodium lauryl sulfate), non-ionic surfactants (e.g., polyoxy-ethylene-sorbitan fatty acid esters [Tween 80 or Tween 60, e.g., from Atlas Powder], polyoxyethylene-castor oil derivatives [HCO-60 or HCO-50 from Nikko Chemicals], or others), polyvinylpyrrolidone, carboxymethylcellulose, lecithin, gelatin, and hyaluronic acid. These emulsifiers (and/or surfactants) can be used independently or in combination. The concentration of surfactant according to the invention impacts microsphere size and can readily be adjusted by one skilled in the art. Preferably the surfactant amount (e.g., optimally the PVA amount) ranges from about 0.01 to about 10% (w/v).

Removal of the organic solvent from the produced O/W emulsion can be carried out by conventional methods. Examples of the removal method of the organic solvent include but are not limited to spray drying, phase separation, and in-water drying. For instance, the removal of the organic solvent can be carried out by evaporating the organic solvent by stirring with a propeller-type stirrer, magnetic stirrer, or the like, optionally under atmospheric pressure, or gradually reducing pressure while controlling degree of vacuum, e.g., by using a rotary evaporator. These methods are routine.

Preferably according to the invention, the organic solvent (e.g., the first organic solvent, the second organic solvent, and/or the third organic solvent) is removed by extraction and evaporation, which further solidifies the microspheres. Optimally this is done by increasing the temperature of the emulsion (i.e., which now comprises microdroplets) to from about 30° C. to about 45° C., and stirring for from about 30 minutes to about 360 minutes. In particular, preferably this is done by increasing the temperature to from about 40° C. to about 42° C., and stirring for from about an hour to about 3 hours, most desirably for about an hour.

The solidified microspheres containing active agent (e.g., drug substance) and release-modifying agent (e.g., arginine) optionally are recovered, for instance, by filtration. If desired, the microspheres further can be dried under vacuum or by freeze-drying.

It goes without saying that the characteristics of the microspheres produced according to the invention may be altered during preparation by manipulating the polymer concentration, reaction temperature, pH, active agent and/or release-modifying agent concentration, and the like. One of ordinary skill in the art would be knowledgeable regarding such manipulations.

In general, although the active agent can be loaded into a preformed microsphere of the invention, it is preferable for the active agent to be loaded into a microsphere of the invention during preparation of the microsphere, especially where a release-modifying agent is further incorporated into the microsphere to stabilize the active agent and to enhance its sustained release.

Pharmaceutical Formulations

The microspheres of the invention (i.e., the microsphere delivery system) optionally comprises a "pharmaceutical formulation" that can be administered intramuscularly, subcutaneously, or orally in the form of suspension in suitable liquid carrier.

Accordingly, also provided by the invention is a method of treating a disease, disorder or condition in a patient (e.g., a human) in need of such treatment. This method comprises use of the pharmaceutical formulation of the invention to administer an active agent to the patient. While any suitable means of administration to a patient can be used within the context of the invention, typically and preferably the inventive method of treating a disease in a patient involves administering the pharmaceutical formulation to a patient via injection. By the term "injection," it is meant that the composition is forcefully introduced into a target tissue of the patient. The composition can be administered to the patient by any suitable route, but preferably is administered to the patient subcutaneously or intramuscularly. When the inventive pharmaceutical formulation is administered by injecting, any suitable injection device can be used. While less preferred, other routes of administration can be used to deliver the composition to the patient in accordance with the inventive method. Indeed, although more than one route can be used to administer the inventive formulation, a particular route can provide a more immediate and more effective reaction than another route.

According to yet another aspect of the invention, a pharmaceutical formulation and a method of producing same are provided. The pharmaceutical formulation optionally includes a container, e.g., containing a single dose of microspheres containing an active agent for treating a condition that is treatable by the sustained release of an active agent from the microspheres. The number of microspheres in the single dose is dependent upon the amount of active agent present in each microsphere and the period of time over which sustained release is desired. Preferably, the single dose is selected to achieve the sustained release of the active agent over a period of from about 1 to about 180 days with the desired release profile.

According to another aspect of the invention, a syringe-containing composition is provided. The composition includes a syringe containing a single dose of microspheres containing an active agent for treating a condition that is treatable by the sustained release of the active agent form the microspheres; and a needle attached to the syringe, wherein the needle has a bore size that is appropriate for introduction of the microspheres. The syringe-containing composition (or other composition according to the invention) also can be used in an alternative to needle injection, e.g., microscission, wherein a stream of gas is fired at the skin creating tiny holes through which the active agent can be delivered.

As indicated above, the microspheres can be prepared to have qualities suitable to be delivered by other parenteral and non-parenteral routes such as oral, buccal, intrathecal, nasal, pulmonary, transdermal, transmucosal and the like.

When used therapeutically, regardless of the route of administration, the microspheres of the invention are administered in therapeutically effective amounts. In general, a "therapeutically effective amount" means an amount effective to deliver a therapeutically effective amount of an amount of active agent, e.g., an amount of active agent necessary to delay the onset of, inhibit the progression of, or halt altogether the particular disease, disorder or condition being treated, or to otherwise provide the desired biological result. Generally, a therapeutically effective amount varies with the patient's age, condition, and gender, as well as the nature and extent of the disease, disorder or condition in the patient, all of which can be determined by one of ordinary skill in the art. The dosage may be adjusted by the individual physician (or veterinarian), particularly in the event of any complication.

A therapeutically effective amount of active agent preferably varies from about 0.0001 mg/kg to about 1000 mg/kg. For certain active agents, the therapeutically effective amount optimally ranges from about 0.1 micrograms/kg to about 1000 micrograms/kg. For other active agents, the therapeutically effective amount optimally ranges from about 0.1 milligrams/kg to about 1000 milligrams/kg. The therapeutic effective amount can be given in one or more dose administrations daily, for one or more days, weekly, monthly, every two or three months, and the like.

The microspheres can be administered alone, or in appropriate combination with other active agents or drug therapies, as part of a pharmaceutical formulation. Such a pharmaceutical formulation may include the microspheres in combination with any standard physiologically and/or pharmaceutically acceptable carriers which are known in the art. The formulation compositions preferably are sterile and contain a therapeutically effective amount of the microsphere in a unit of weight or volume suitable for administration to a patient. The term "pharmaceutically-acceptable carrier" as used herein means one or more compatible solid or liquid filler, diluents or encapsulating substances which are suitable for administration into a human or other animal. The term "carrier" denotes an organic or inorganic ingredient, natural or synthetic, and combinations thereof, with which the active ingredient is combined to facilitate the application. The components of the pharmaceutical formulation preferably are capable of being co-mingled with the components of the present invention (e.g., the active agent, the biodegradable polymer, and the release-modifying agent), and with each other, in a manner such that there is no interaction which would substantially impair the desired pharmaceutical efficacy. Pharmaceutically acceptable carrier further means a non-toxic material that is compatible with a biological system such as a cell, cell culture, tissue, or organism. The characteristics of the carrier depend on the route of administration. Physiologically and pharmaceutically acceptable carriers include diluents, fillers, salts, buffers, stabilizers, desiccants, bulking agents, propellants, acidifying agents, coating agents, solubilizers, and other materials which are well known in the art. Carrier formulations suitable for oral, subcutaneous, intravenous, intramuscular, or other type of administrations also are well known, and can be found, e.g., in Remington's Pharmaceutical Sciences (Mack Publishing Co., Easton, Pa.), as well as in other sources.

Preparations for parenteral administration preferably include but are not limited to sterile aqueous or non-aqueous solutions, suspensions, and emulsions. Examples of solvents include propylene glycol, polyethylene glycol, vegetable oils such as olive oil, injectable organic esters such as ethyl oleate, and the like. Aqueous carriers include water, salts and buffer solutions such as saline and buffered media, alcoholic/aqueous solutions and emulsions or suspensions, as well as others. Parenteral vehicles include but are not limited to Normal Saline (0.9% sodium chloride), ½ Normal Saline (0.45% sodium chloride), 5% Dextrose in Water, Lactated Ringer's Solution, 5% Dextrose in ½ Normal Saline with 20 mEq KCl, 5% Dextrose in Lactated Ringer's Solution, 5% Dextrose in ⅓ Normal Saline, 5% dextrose in ½ Normal Saline, Normosol®-M in 5% Dextrose, Normosol®-R in 5% Dextrose, as well as others. Intravenous vehicles include fluid and nutrient replenishers, electrolyte replenishers (such as those based on Ringer's dextrose), and the like. Preservatives and other additives also optionally can be present such as, for example, antimicrobials, anti-oxidants, chelating agents, and inert gases and the like, so long as these additional ingredients do not deleteriously impact the advantageous properties of the microspheres. Generally, the microspheres can be administered to the subject (any mammalian recipient) using the same modes of administration that currently are used for microsphere and/or microparticle therapy in humans.

Whether comprising a pharmaceutical formulation or not, the microspheres of the invention are useful for a wide variety of separations, diagnostic, therapeutic, industrial, commercial, cosmetic, and research purposes. Thus, the microspheres of the invention are useful for medical and diagnostic applications, such as drug delivery, vaccination, gene therapy, and histopathological or in vivo tissue or tumor imaging.

For example, for in vivo diagnostic purposes, the microspheres can include a macromolecule such as an immunoglobulin or cell receptor labeled with a detectable label. Administration of the labeled microsphere to a patient creates an imaging agent for the diagnosis of a proliferative disorder such as cancer or infection, or as a tool for the evaluation of the success of a therapeutic agent in reducing the proliferation of a particular adverse cell or organism.

For in vitro diagnosis, microspheres containing a macromolecule such as an immunoglobulin, cell receptor, or oligonucleotide probe specific for the cell or organism under investigation, can be combined with a test sample, the microspheres separated from any non-bound components of the sample, and then the bound molecules detected by conventional methods.

The microspheres moreover are useful as therapeutic agents and enable the use of alternative routes of administration, for instance, when the microspheres include an active agent that is a therapeutic drug, and are administered to a patient for the sustained release of the active agent to the site requiring therapy. The microspheres also are useful as therapeutic or prophylactic agents, for example, when the microspheres include a macromolecule that is itself a therapeutic or prophylactic agent, such as an enzyme or immunoglobulin. The sustained release of such therapeutic agents is particularly useful for therapeutic proteins or peptides having short half-lives that must be administered by injection.

The microspheres additionally are useful, among other things, for the purification of molecules from a complex mixture, as a reagent for the detection or quantification of a specific molecule, or for the production of molecules, such as antibodies. For example, microspheres containing a macromolecule, such as an immunoglobulin, can be attached to a chromatography column and used in immunoaffinity chromatography to separate a ligand from a complex mixture. Alternately, microspheres including a labeled macromolecule or a mixture of labeled macromolecules specific for different cells or biomolecules, such as cell receptors, can be used to detect changes in the number of cells or biomolecules in response to a particular test condition, using techniques, e.g., such as flow cytometry.

Furthermore, the microspheres optionally can be used as adjuvants for vaccine production wherein antigen-containing microspheres are injected into a research animal, such as a mouse or rabbit, to trigger an enhanced immune response for the production of antibodies to the antigen.

Additional commercial uses include the formation of enzyme particles for addition to detergents, cosmetics, lotions or creams, inks and paints. Other uses would be apparent to one skilled in the art in view of the teaching provided herein.

The following examples further illustrate the invention (e.g., by showing particular ways of preparing and evaluating the microspheres of the invention) but, of course, should not be construed as in any way limiting its scope.

EXAMPLE 1

This example describes the effect of arginine on the interaction between biodegradable polymer and salmon calcitonin. For the experiments described herein, although arginine is combined with acetic acid, for convenience in describing the results obtained, frequently only the arginine is mentioned.

For these studies, 5 mL of salmon calcitonin solution (1 mg/mL) containing arginine (0.6 mg/mL) and glacial acetic acid (3 mg/mL) in 10 mM phosphate buffer was prepared and mixed with 100 mg of blank poly(D,L-lactide-co-glycolide) (PLGA) microspheres ("Arginine" sample). The blank microspheres were prepared as follows. Briefly, 2.0 g of 50:50 poly(D,L-lactide-co-glycolide) (PLGA) polymer having an inherent viscosity of 0.4 dl/g (Resomer RG503H from Boehringer Ingelheim), was dissolved in 8.0 g dichloromethane ($CH_2Cl_2$). The polymer solution was then mixed with 2 mL of methanol. The organic phase containing polymer was dispersed into 400 mL of 0.35% polyvinyl alcohol (PVA) dissolved in water using a Silverson Lab mixer. The organic solvents were extracted and evaporated by increasing the temperature to 40° C. and stirring for 1 hour at this temperature. The microspheres were obtained by filtration, washed and then freeze-dried. The average volume particle size of the microspheres obtained was 39 µm.

For a comparative sample ("Arginine-Free" sample), 5 mL of salmon calcitonin solution (1 mg/mL) in 10 mM phosphate buffer, without arginine and glacial acetic acid, was prepared and mixed with 100 mg blank poly(D,L-lactide-co-glycolide) (PLGA) microspheres. Also, a 1 mg/mL salmon calcitonin solution containing arginine (0.6 mg/mL) and glacial acetic acid (3 mg/mL) but not any microspheres was prepared as the control for "Arginine" sample, and a 1 mg/mL salmon calcitonin solution, without arginine and glacial acetic acid, in 10 mM phosphate buffer was prepared as a control for "Arginine-Free" sample.

The microsphere-containing Arginine and Arginine-free samples and their respective microsphere-free control solutions were stored at 37° C. After the separation of solution from microspheres, the concentration of salmon calcitonin in the separated solution obtained from the Arginine and Arginine-free samples was determined by HPLC at 1, 3, and 7 days of storage. The salmon calcitonin concentration of the microsphere-free control solutions also was determined at the same intervals. The percent of salmon calcitonin bound to (or interacted with) the microspheres was calculated using the reduced salmon calcitonin concentration in the Arginine and Arginine-free samples compared to the corresponding microsphere-free control solutions. The results are shown in Table 1.

TABLE 1

% Salmon Calcitonin Interacted with PLGA microspheres

| Time (day) | Arginine-Free | 0.6 mg/mL Arginine |
|---|---|---|
| 1 | 11.1 ± 2.4% | 1.3 ± 1.0% |
| 3 | 32.1 ± 5.0% | 1.5 ± 0.5% |
| 7 | 57.1 ± 9.3% | 3.4 ± 0.5% |

As can be seen from Table 1, the presence of arginine reduced the interaction between salmon calcitonin and PLGA significantly as compared to the arginine-free samples.

EXAMPLE 2

This example describes the effect of arginine on the stability of salmon calcitonin.

The stability of salmon calcitonin in the Arginine and Arginine-free samples from Example 1 was determined by HPLC. The percent stability was determined as the peak area of salmon calcitonin divided by the total peak area obtained for the solution. The results are shown in Table 2.

TABLE 2

% Salmon Calcitonin Stability

| Time (day) | Arginine-Free | 0.6 mg/mL Arginine |
|---|---|---|
| 1 | 80.4 ± 1.5% | 95.2 ± 0.6% |
| 3 | 55.4 ± 2.6% | 94.5 ± 0.5% |
| 7 | 20.7 ± 3.4% | 92.4 ± 0.5% |

As can be seen from Table 2, the salmon calcitonin was well-protected by arginine, as confirmed by its increased stability in the presence of arginine as compared to in the arginine-free samples. These results are consistent with peptide degradation occurring in the arginine-free samples.

EXAMPLE 3

This example describes the preparation and characterization of salmon calcitonin-loaded PLGA microspheres containing arginine.

For these studies, 0.942 g of 50:50 poly(D,L-lactide-co-glycolide) (PLGA) polymer having an inherent viscosity of 0.4 dl/g (Resomer RG503H from Boehringer Ingelheim) was dissolved in 3.740 g dichloromethane ($CH_2Cl_2$). Arginine (2 g) was dissolved in 10 mL of glacial acetic acid. Salmon calcitonin acetate (60.52 mg) was dissolved in 1 mL of methanol. The polymer solution was mixed with the salmon calcitonin solution, and then mixed with 30 µL of arginine solution. The organic phase containing arginine, salmon calcitonin and polymer was dispersed into 400 mL of 0.35% polyvinyl alcohol (PVA) dissolved in water, using a Silverson Lab mixer. The organic solvents were extracted and evaporated by increasing the temperature to 42° C. and stirring for 1 hour at this temperature. The microspheres were obtained by filtration, washed, and then freeze-dried. The average volume particle size of microspheres obtained was 60 µm. The salmon calcitonin content was 4.02%, and the salmon calcitonin loading efficiency was 79.8%. The arginine content was 0.61%, and the arginine loading efficiency was 102.0%.

EXAMPLE 4

This example describes the preparation and characterization of arginine-free salmon calcitonin-loaded PLGA microspheres.

For these studies, 0.942 g of 50:50 poly(D,L-lactide-co-glycolide) (PLGA) polymer having an inherent viscosity of 0.4 dl/g (Resomer RG503H from Boehringer Ingelheim) was dissolved in 3.760 g dichloromethane ($CH_2Cl_2$). Salmon calcitonin acetate (59.65 mg) was dissolved in 1 mL of methanol. The polymer solution was mixed with the salmon calcitonin solution. The organic phase containing salmon calcitonin and polymer was dispersed into 400 mL of 0.35% polyvinyl alcohol (PVA) dissolved in water, using Silverson Lab mixer. The organic solvents were extracted and evaporated by increasing the temperature to 42° C. and stirring for 1 hour at this temperature. The microspheres were obtained by filtration, washed, and then freeze-dried. The average volume particle size of microspheres was 52 µm. The salmon calcitonin content was 4.70%, and the salmon calcitonin loading efficiency was 95.1%.

EXAMPLE 5

This example describes the in vitro release of the arginine-containing salmon calcitonin-loaded microspheres as compared to the arginine-free salmon calcitonin-loaded microspheres.

For these studies, about 10 mg of the salmon calcitonin-loaded microspheres prepared as described in Examples 3 and 4 were dispersed in 1 mL of in vitro release medium, 10 mM acetate buffer, pH 4.0, at 37° C. At predetermined time intervals, the sample tubes were removed from the 37° C. incubator and centrifuged to separate microspheres and release medium. The separated microspheres were dissolved in 90% acetonitrile and the total peptide remaining in the microspheres was determined by HPLC. The data are presented in Table 3.

TABLE 3

% Cumulative In Vitro Release of Salmon Calcitonin

| Time (day) | Arginine-Free | 0.6% Arginine-Loaded |
|---|---|---|
| 0 | 0.0 | 0.0 |
| 1 | 5.7 | 2.3 |
| 3 | 16.1 | 7.8 |
| 7 | 15.7 | 7.3 |
| 14 | 21.4 | 33.5 |
| 21 | 25.9 | 72.2 |
| 28 | 86.7 | 83.2 |
| 42 | 99.4 | 95.5 |

As can be seen from Table 3, the arginine-loaded microspheres showed lower initial release between 0 and 7 days as compared to the arginine-free microspheres. This was followed by a more linear sustained release between 7 and 42 days from the arginine-loaded microspheres compared to the arginine-free microspheres. The arginine-loaded microspheres gave more gradual in vitro release than the arginine-free microspheres.

EXAMPLE 6

This example describes the peptide stability in microspheres.

The stability of salmon calcitonin in the microspheres prepared as described in Examples 3 and 4 was evaluated during the in vitro release as described in Example 5. For these studies, about 10 mg of microspheres were dispersed in 10 mM acetate buffer, pH 4.0, at 37° C. At predetermined time intervals, the sample tubes were removed from the 37° C. incubator and centrifuged to separate microspheres and release medium. The separated microspheres were dissolved in 90% acetonitrile and the stability of salmon calcitonin was determined by HPLC by comparing the purity of salmon calcitonin at any time point to the purity at time zero. The data are presented in Table 4.

TABLE 4

% Relative Stability of Salmon Calcitonin

| Time (day) | Arginine-Free | 0.6% Arginine-Loaded |
|---|---|---|
| 0 | 100.0 | 100.0 |
| 1 | 91.5 | 96.0 |
| 3 | 87.9 | 95.4 |
| 7 | 83.5 | 91.9 |
| 14 | 89.3 | 94.5 |

As shown from the data in Table 4, the arginine-loaded microspheres showed a greater salmon calcitonin stability as compared to the arginine-free microspheres. The arginine-loaded microspheres stabilized the incorporated peptide in the polymer matrix during in vitro release.

EXAMPLE 7

This example describes the change of the physical property of the PLGA polymer caused by the interaction between arginine and polymer.

The glass transition temperature (Tg) of arginine-loaded PLGA microspheres was determined to evaluate the effect of arginine loading on the physical property of PLGA polymer matrix by differential scanning calorimetry (DSC). 0.6% arginine-loaded PLGA microspheres were heated from 25° C. to 100° C. at 5° C./min, and the thermogram was analyzed for the glass transition. Arginine-free blank PLGA microspheres also were analyzed as the comparative sample. A Tg of 56.1° C. was observed for the arginine-loaded microspheres. By comparison, a Tg of 51.1° C. was observed for the arginine-free microspheres.

The fact that the arginine-loaded microspheres showed about a 5° C. higher transition temperature as compared to the blank microspheres confirms that an interaction is taking place between arginine and PLGA polymer in the microspheres. This further suggests that the release modifying agent modulates the interaction between the polymer and the active agent. Specifically, this suggests that when release modifying agent is present in the microspheres, the release modifying agent interacts with the PLGA polymer instead of the active agent interacting with the polymer, and the release modifying agent thus reduces the interaction of active agent with the polymer.

EXAMPLE 8

This example describes the preparation and characterization of Octreotide-loaded PLGA microspheres containing release-modifying agent (arginine with glacial acetic acid).

In two separate studies, 0.948 g (study 1) or 0.946 g (study 2) of 50:50 poly(D,L-lactide-co-glycolide) (PLGA) polymer having an inherent viscosity of 0.4 dl/g (Resomer RG503H from Boehringer Ingelheim) was dissolved in 3.853 g (study 1) or 3.874 g (study 2) dichloromethane $CH_2Cl_2$. Arginine (2 g) was dissolved in 10 mL of glacial acetic acid. Octreotide acetate (58.98 mg, study 1; 57.61 mg study 2) was dissolved in 1 mL of methanol. The polymer solution was mixed with the Octreotide solution, and then mixed with 30 µL of arginine solution. The organic phase containing arginine, glacial acetic acid, Octreotide, and polymer was dispersed into 200 mL of 0.35% polyvinyl alcohol (PVA) dissolved in water, using a Silverson Lab mixer. The organic solvents were extracted and evaporated by increasing the temperature to 42° C. and stirring for 1 hour at this temperature. The microspheres were obtained by filtration, washed, and then freeze-dried. The average volume particle size of microspheres was 41 µm (study 1) or 49 µm (study 2). The Octreotide content was 4.31% (study 1) or 4.3% (study 2), and the octreotide loading efficiency was 84.5% (study 1).

EXAMPLE 9

This example describes the preparation and characterization of octreotide-loaded PLGA microspheres not containing any release-modifying agent.

For these studies, 0.950 g of 50:50 poly(D,L-lactide-co-glycolide) (PLGA) polymer having an inherent viscosity of 0.4 dl/g (Resomer RG503H from Boehringer Ingelheim) was dissolved in 3.802 g dichloromethane (CH2Cl2). Octreotide acetate (57.69 mg) was dissolved in 1 mL of methanol. The polymer solution was mixed with the octreotide solution and then mixed with 30 mL of glacial acetic acid solution. The organic phase was dispersed into 100 mL of 0.35% polyvinyl alcohol (PVA) dissolved in water using a Silverson Lab mixer. The organic solvents were extracted and evaporated by increasing the temperature to 42° C. and stirring for 1 hour at this temperature. The microspheres were obtained by filtration, and then washed and dried. The octreotide content was 3.27%.

EXAMPLE 10

This example describes the pH versus stability profile of the exemplary target active drug, octreotide acetate.

For this study, 0.2 mg/mL octreotide acetate solutions in different pH buffers (buffer ionic strength=~50 mM) were incubated at 70° C. At various designated times, the concentration of octreotide was determined using HPLC. The degradation rate versus time (Kobs) was calculated and plotted. Based on the results obtained (presented in Table 5 below), octreotide acetate appears relatively stable between a pH of 3.0 and 5.0.

TABLE 5

Accelerated stability of octreotide solutions at various pHs

| pH/Buffers | Octreotide Assay | Time | | | |
|---|---|---|---|---|---|
| | | 0 hours | 24 hours | 48 hours | 69 hours |
| pH 2.0, Glycine-HCl | mg/mL | 0.1965 | 0.1651 | 0.1425 | 0.1303 |
| | (% Stability) | (100.00) | (84.02) | (72.52) | (66.31) |

TABLE 5-continued

Accelerated stability of octreotide solutions at various pHs

| pH/Buffers | Octreotide Assay | Time | | | |
|---|---|---|---|---|---|
| | | 0 hours | 24 hours | 48 hours | 69 hours |
| pH 3.0, Glycine-HCl | mg/mL | 0.2214 | 0.2136 | 0.2050 | 0.2004 |
| | (% Stability) | (100.00) | (96.48) | (92.59) | (90.51) |
| pH 4.0, Arginine-Acetate | mg/mL | 0.1911 | 0.1860 | 0.1784 | 0.1741 |
| | (% Stability) | (100.00) | (97.33) | (93.35) | (91.10) |
| pH 5.0, Arginine-Acetate | mg/mL | 0.2027 | 0.1975 | 0.1848 | 0.1819 |
| | (% Stability) | (100.00) | (97.43) | (91.17) | (89.74) |
| pH 6.0, Phosphate | mg/mL | 0.1934 | 0.1738 | 0.1434 | 0.1276 |
| | (% Stability) | (100.00) | (89.87) | (74.15) | (65.98) |
| pH 7.0, Phosphate | mg/mL | 0.2047 | 0.1638 | 0.1247 | 0.1056 |
| | (% Stability) | (100.00) | (80.02) | (60.92) | (51.59) |
| pH 8.0, Phosphate | mg/mL | 0.1906 | 0.0793 | 0.0369 | 0.0280 |
| | (% Stability) | (100.00) | (41.61) | (19.36) | (14.69) |

EXAMPLE 11

This example describes the pH profile of the aqueous extract of the octreotide microspheres containing release-modifying agent (arginine and glacial acetic acid), and the pH profile of the in vitro release medium incubated at 55° C. with 10 mg microspheres/mL. This example also describes the pH profile of the aqueous extract of the octreotide microspheres not containing any release-modifying agent, and the pH profile of the in vitro release medium. This example further compares the pH profiles obtained for octreotide microspheres containing or not containing any release-modifying agent.

For these studies, 50 mg of octreotide acetate-loaded microspheres containing the release-modifying agent were prepared as described in Example 8, and octreotide acetate-loaded microspheres not containing the release-modifying agent were prepared as described in Example 9. The microsphere were incubated in 5 mL of purified water at 55° C. The release medium was separated from the microspheres at various designated times, and the remaining microspheres were washed with water. The pH of the release medium was measured. Also, the aqueous extract of the microspheres was prepared by dissolving the remaining microspheres using 2 mL dichloromethane and extracting with 5 mL purified water. The pH of the aqueous extract, which represents the pH of the microspheres, was measured. The pH profile of the release medium and the aqueous extract of the microspheres was obtained by plotting time vs. pH. The data obtained are presented in Table 6.

TABLE 6 pH profiles of release media and microsphere extracts for microspheres containing or not containing release-modifying agent

| Microsphere | Sample | Time | | | |
|---|---|---|---|---|---|
| | | 0 days | 1 days | 2 days | 4 days |
| 0.6% Arginine-Loaded | (Release Media) | (5.67) | (3.55) | (3.24) | (2.54) |
| | Microsphere Extract | 5.06 | 4.02 | 3.63 | 3.47 |
| Arginine-Free | (Release Media) | (5.69) | (3.61) | (3.09) | (2.47) |
| | Microsphere Extract | 6.61 | 4.41 | 3.68 | 3.06 |

As can be seen from Table 6, with regard to the octreotide acetate-loaded microspheres containing the release-modifying agent, the pH of the release medium of the microspheres decreased rapidly from a pH of about 5.7 to a pH of about 3.6 within the first 24 hours, and further decreased to a pH of about 2.5 by 4 days. This rapid and pronounced change likely was due to the acidic degradants of PLGA polymer. In contrast, the pH change of the aqueous extract of the microspheres containing the release-modifying agent was relatively minimal over the same course of time. Specifically, the aqueous extract decreased from a pH of about 5.0 to a pH of about 4.0 within the first 24 hours, and further decreased to a pH of about 3.5 by 4 days.

As further can be seen from Table 6, with regard to the octreotide acetate-loaded microspheres not containing the release-modifying agent, the profile of its release medium was very similar to the profile obtained for the release medium of octreotide acetate-loaded microspheres containing the release-modifying agent. Specifically, for microspheres not containing the release-modifying agent, the pH decreased rapidly from a pH of about 5.7 to a pH of about 3.6 within the first 24 hours, and further decreased to a pH of about 2.5 by 4 days, likely due to the acidic degradants of the PLGA polymer. By comparison, the pH change of aqueous extract of the microspheres not containing the release-modifying agent was much greater than that observed for the aqueous extract of the octreotide acetate-loaded microspheres containing the release-modifying agent. Specifically, the pH decreased dramatically from about 6.6 to about 4.5 within the first 24 hours, and further decreased to a pH of about 3.0 by 4 days.

These results confirm that the minimal pH change in the aqueous extract of the microspheres containing the release-modifying agent appears to be due to the benefits of the release-modifying agent employed. This release-modifying agent, a mixture of arginine and glacial acetic acid, thus appears to function as a pH-stabilizing agent. The pH was maintained within the optimum stability pH range of the target active agent, octreotide acetate, i.e., at a pH of between 3.0 and 5.0. In distinct contrast, for microspheres not containing the release-modifying agent the pH started at outside the optimal range (i.e., a pH of about 6.6) and rapidly decreased.

EXAMPLE 12

This example describes the quantitation of the in vitro release of the octreotide-loaded microspheres containing release-modifying agent (arginine and glacial acetic acid) as compared to the octreotide-loaded microspheres not containing any release-modifying agent.

For these studies, about 50 mg of microspheres were dispersed into 5 mL of purified water (the release medium) at 55°

C. The sample tubes were removed from the 55° C. incubator at various designated times, and were centrifuged to separate microspheres and release medium. The concentration of octreotide released from microspheres was determined by HPLC, and calculated as % release. The data obtained are presented in Table 7.

TABLE 7

% Cumulative In Vitro Release of Octreotide

| Time (day) | 0.6% Arginine-Loaded | Arginine-Free |
|---|---|---|
| 0 | 0 | 0 |
| 0.04 | 1.0 | 39.7 |
| 1 | 11.1 | 49.8 |
| 2 | 27.9 | 86.6 |
| 4 | 93.3 | 97.5 |

As can be seen from Table 7, for microspheres not containing the release-modifying agent, a very rapid burst was observed, up to 40% release within about an hour, about 50% release by Day 1, about 87% release by Day 2, and roughly 100% release by Day 4. By comparison, for microspheres containing the release-modifying agent, release was steady and prolonged, without a significant initial burst. Specifically, about 10% release was observed by Day 1, about 30% release by Day 2, and roughly 95% release by Day 4.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Accordingly, this invention includes all modifications encompassed within the scope of the invention as defined by the following claims.

What is claimed is:

1. A process for preparing a microsphere delivery system comprising:
    (a) dissolving a biodegradable polymer in a first organic solvent that is immiscible with water to produce a first mixture;
    (b) dissolving an active agent in a second organic solvent that is miscible with water to produce a second mixture, wherein the active agent is a protein or a peptide;
    (c) producing a third mixture by separately dissolving a basic amino acid in either (i) a third organic solvent that is miscible with water, or (ii) a mixture of said second organic solvent and said third organic solvent, wherein said basic amino acid is selected from the group consisting of arginine, lysine, and histidine, and wherein said second organic solvent and said third organic solvent are different;
    (d) mixing together said first mixture, said second mixture and said third mixture to prepare a homogeneous organic dispersed phase;
    (e) emulsifying said homogeneous organic dispersed phase to produce microdroplets; and
    (f) removing said first organic solvent, said second organic solvent, and said third organic solvent from said microdroplets to produce said microspheres.

2. The process according to claim 1, wherein the emulsification is done in an aqueous continuous phase comprising a surfactant.

3. The process according to claim 1, wherein the emulsification is done in an aqueous continuous phase comprising polyvinyl alcohol in water.

4. The process according to claim 1, wherein said first organic solvent, said second organic solvent, and said third organic solvent are removed by extraction and evaporation.

5. The process according to claim 1, wherein said first organic solvent, said second organic solvent, and said third organic solvent are removed by increasing the temperature of said microdroplets to from about 30° C. to about 45° C., and stirring for from about 30 minutes to about 360 minutes.

6. The process according to claim 1, further comprising recovering said microspheres.

7. The process according to claim 6, wherein said microspheres are recovered by filtration.

8. The process according to claim 1, wherein said microsphere delivery system is a pharmaceutical formulation for injection.

9. The process according to claim 1, wherein said first solvent comprises dichloromethane or chloroform.

10. The process according to claim 1, wherein said second solvent comprises methanol or ethanol.

11. The process according to claim 1, wherein said third solvent comprises acetic acid and methanol.

12. The process according to claim 1, wherein said biodegradable polymer is selected from the group consisting of polylactic acid, polyglycolic acid, and copolymers of lactic acid and glycolic acid.

13. The process according to claim 1, wherein said active agent is a therapeutic agent.

14. The process according to claim 1, wherein said active agent is a diagnostic agent.

15. The process according to claim 1, wherein said active agent is selected from the group consisting of hormones, antibiotics, antineoplastics, anesthetics, anti-psychotics, anticoagulants, vasoactive agents, neuroactive agents, immunomodulating agents, antivirals, antibodies, and antigens.

16. The process according to claim 1, wherein said active agent is a peptide.

17. The process according to claim 1, wherein said active agent is selected from the group consisting of salmon calcitonin, leuprolide, and octreotide.

18. The process according to claim 1, wherein said active agent is goserelin.

19. The process according to claim 1, wherein said basic amino acid is L-arginine.

20. The process according to claim 19, wherein step (c) further comprises dissolving glacial acetic acid in the third organic solvent or the mixture of said second organic solvent and said third organic solvent.

21. The process according to claim 1, wherein step (c) further comprises dissolving an organic acid in the third organic solvent or the mixture of said second organic solvent and said third organic solvent.

22. The process according to claim 21, wherein the amount of said basic amino acid comprises from about 0.1 to 1.0% (w/w) of said microsphere delivery system.

\* \* \* \* \*